(12) United States Patent
Brennan et al.

(10) Patent No.: US 9,417,463 B2
(45) Date of Patent: Aug. 16, 2016

(54) LENS DESIGN AND METHOD FOR MINIMIZING VISUAL ACUITY VARIATION EXPERIENCED BY MYOPIA PROGRESSORS

(71) Applicant: Johnson & Johnson Vision Care, Inc., Jacksonville, FL (US)

(72) Inventors: Noel A. Brennan, Ponte Vedra Beach, FL (US); Khaled A. Chehab, Jacksonville, FL (US); Jeffrey H. Roffman, St. Johns, FL (US); Xin Wei, Arlington, TX (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 114 days.

(21) Appl. No.: 14/464,267

(22) Filed: Aug. 20, 2014

(65) Prior Publication Data

US 2016/0054586 A1 Feb. 25, 2016

(51) Int. Cl.
*G02C 7/04* (2006.01)
*A61F 2/14* (2006.01)
*A61F 2/16* (2006.01)
*G02C 7/06* (2006.01)

(52) U.S. Cl.
CPC .............. *G02C 7/041* (2013.01); *A61F 2/145* (2013.01); *A61F 2/1656* (2013.01); *G02C 7/044* (2013.01); *G02C 7/06* (2013.01); *G02C 2202/24* (2013.01)

(58) Field of Classification Search
CPC ............ G02C 7/041; G02C 7/06; G02C 7/04; A61F 2/145
USPC .................. 351/159, 159.06, 159.01–159.02, 351/159.19
See application file for complete search history.

(56) References Cited

U.S. PATENT DOCUMENTS

| 5,225,858 A | 7/1993 | Portney |
| 6,752,499 B2 * | 6/2004 | Aller ......................... G02C 7/04 351/159.06 |

(Continued)

FOREIGN PATENT DOCUMENTS

| EP | 2762953 A1 | 8/2014 |
| WO | WO2005040895 A1 | 5/2005 |

OTHER PUBLICATIONS

Thibos, L, et al, "Accuracy and Precision of Objective Refraction From Wavefront Aberrations", Journal of Vision, vol. 4, pp. 329-351 (2004).

*Primary Examiner* — Scott J Sugarman
*Assistant Examiner* — Kristina Deherrera
(74) *Attorney, Agent, or Firm* — Carl J. Evens (57) ABSTRACT

Contact lenses incorporate power profiles that minimize visual acuity variation for progressing myopes based upon minimization of the variation of neural sharpness image quality over a specific time period. The contact lens includes a center and at least one peripheral zone surrounding the center and having a different dioptric power than at the center. The lens has power profile selected from the group consisting of a power profile with spherical aberration, a multifocal power profile, a freeform power profile, and a segmented freeform power profile. The power profile is based on an initial paraxial power of a myopia progressor and a defined myopia progression rate over a specific time period, resulting in controlled change of the neural sharpness, thereby minimizing changes in changes in visual acuity at a beginning of the time period and at an end of the time period.

23 Claims, 7 Drawing Sheets

(56) References Cited

U.S. PATENT DOCUMENTS

| | | | |
|---|---|---|---|
| 8,485,662 B2 * | 7/2013 | Collins | G02C 7/04 351/159.18 |
| 8,998,408 B2 * | 4/2015 | Wei | G02C 7/04 351/159.6 |
| 2009/0244478 A1 | 10/2009 | Wooley | |
| 2010/0073629 A1 | 3/2010 | Menezes | |
| 2010/0328604 A1 * | 12/2010 | Collins | G02C 7/04 351/159.06 |
| 2012/0327363 A1 | 12/2012 | Wooley | |
| 2013/0182216 A1 | 7/2013 | Ho | |
| 2013/0278888 A1 | 10/2013 | Bakaraju | |

* cited by examiner

LENS DESIGN AND METHOD FOR MINIMIZING VISUAL ACUITY VARIATION EXPERIENCED BY MYOPIA PROGRESSORS

BACKGROUND OF THE INVENTION

1. Field of the Invention

The present invention relates to ophthalmic lenses. More particularly, the present invention is directed to ophthalmic lenses having power profiles that provide foveal vision correction and minimize visual acuity variation experienced by progressing myopes over the course of time.

2. Discussion of the Related Art

Common conditions which lead to reduced visual acuity include myopia and hyperopia, for which corrective lenses in the form of spectacles, or rigid or soft contact lenses, are prescribed. The conditions are generally described as the imbalance between the length of the eye and the focus of the optical elements of the eye, myopic eyes focusing in front of the retinal plane and hyperopic eyes focusing behind the retinal plane. Myopia typically develops because the axial length of the eye grows to be longer than the focal length of the optical components of the eye, that is, the eye grows too long. Hyperopia typically develops because the axial length of the eye is too short compared with the focal length of the optical components of the eye, that is, the eye does not grow long enough.

Myopia has a high prevalence rate in many regions of the world. Of greatest concern with this condition is its possible progression to high myopia, for example greater than five (5) or six (6) diopters, which dramatically affects one's ability to function without optical aids. High myopia is also associated with an increased risk of retinal disease, cataracts, and glaucoma.

Corrective lenses are used to alter the gross focus of the eye to render a clearer image at the retinal plane, by shifting the focus from in front of the plane to correct myopia, or from behind the plane to correct hyperopia, respectively. However, the corrective approach to the conditions does not address the cause of the condition, but is merely prosthetic or intended to address symptoms. Moreover, conventional corrective approaches for spherical equivalent power, such as spectacles and contact lenses, are effective at correcting the static focus error, but do not address the dynamic change in gross focus error over time, resulting in poor vision outcome shortly after the dispensing of lenses.

Most eyes do not have simple myopia or hyperopia, but have myopic astigmatism or hyperopic astigmatism. Astigmatic errors of focus cause the image of a point source of light to form as two mutually perpendicular lines at different focal distances. In the following discussion, the terms myopia and hyperopia are used to include simple myopia or myopic astigmatism and hyperopia and hyperopic astigmatism respectively.

Over the course of a year, young myopes usually progress toward more severe myopia. The progression rate typically ranges from about −0.25 D/year to about −0.75 D/year. If a conventional optical correction (e.g., with spherical spectacle glasses) is prescribed for a progressing myope to provide optimal distance vision correction at the beginning of the year, then at the end of the year, the patient may experience mild-to-severe blurry distance vision. The present invention seeks to provide lens designs that minimize such a variation in vision and prolong the period before the subject feels the need for a new prescription.

SUMMARY OF THE INVENTION

The lens designs of the present invention overcomes the limitations of the prior art by ensuring comparable or better distance vision correction with minimization of visual acuity variation experienced by progressing myopes over the course of time.

In accordance with one aspect, the present invention is directed to an ophthalmic lens for minimizing visual acuity variation for a progressing myope. The lens comprises a lens having a center and at least one peripheral zone surrounding the center and having a different dioptric power than at the center. The lens has power profile selected from the group consisting of a power profile with spherical aberration, a multifocal power profile, a freeform power profile, and a segmented freeform power profile. The power profile is determined based on an initial paraxial power of a myopia progressor and a defined myopia progression rate over a specific time period, so that changes in visual acuity at a beginning of the time period and at an end of the time period are minimized.

In accordance with another aspect, the present invention is directed to a method for minimizing visual acuity variation for a progressing myope. An ophthalmic lens is provided having a center and at least one peripheral zone surrounding the center and having a different dioptric power than at the center. The power profile of the lens is selected from the group consisting of a power profile with spherical aberration, a multifocal power profile, a freeform power profile, and a segmented freeform power profile. The power profile of the lens is determined based on a paraxial power of a myopia progressor and a defined myopia progression rate over a specific time period, so that changes in visual acuity at a beginning of the time period and at an end of the time period are minimized.

The contact lens of the present invention is designed with a power profile to minimize visual acuity variation experienced by progressing myopes over the course of time.

The lens design of the present invention may also be customized to achieve both good foveal vision correction and minimal variation of visual performance over time based on the subject eyes' average pupil size.

The contact lens design of the present invention provides a simple, cost-effective and efficacious means and method for correcting myopia for progressing myopes whose rates are increasing throughout the world.

BRIEF DESCRIPTION OF THE DRAWINGS

The foregoing and other features and advantages of the invention will be apparent from the following, more particular description of preferred embodiments of the invention, as illustrated in the accompanying drawings.

DETAILED DESCRIPTION OF THE INVENTION

Myopes usually progress toward more severe myopia over the course of time. According to the present invention, lens designs are provided having a center and at least one peripheral zone surrounding the center and having a different dioptric power than at the center. The lens designs may have a variety of power profiles including, but not limited to, spherical lenses, lenses having spherical aberration, multifocal lenses, freeform lenses, segmented freeform lenses, and the like. According to the present invention, the power profiles minimize changes in visual acuity variation, as measured by neural sharpness, over a specific period of time at a defined myopia progression rate.

According to the present invention, a myopia progression rate may be selected based at least one factor such as gender, age, ethnicity, family history, or any combination thereof. In specific embodiments, the myopia progression rate may range from about −0.25 D/year to about −0.75 D/year. Prevalence, incidence and progression rates of myopia are well published in epidemiology studies and can be found in literature such as the Journal of Investigative Ophthalmology and Visual Science, IVOS.org.

Retinal image quality at various stages of myopia progression, as measured by neural sharpness, is calculated based upon four factors: entrance pupil size (EP), refractive error (Rx), optics of the eye, and optics of a lens.

Neural sharpness is given by the following equation:

$$NS = \frac{\int_{-\infty}^{\infty}\int_{-\infty}^{\infty} psf(x,y) g_N(x,y) dx dy}{\int_{-\infty}^{\infty}\int_{-\infty}^{\infty} psf_{DL}(x,y) g_N(x,y) dx dy},\quad (1)$$

wherein psf or point-spread function is the image of a point object and is calculated as the squared magnitude of the inverse Fourier transform of the pupil function P(X,Y) where P(X,Y) is given by $$P(X,Y)=A(X,Y)\exp(ikW(X,Y)), \quad (2)$$

wherein k is the wave number (2π/wavelength) and A(X, Y) is an optical apodization function of pupil coordinates X,Y, $psf_{DL}$ is the diffraction-limited psf for the same pupil diameter, and $g_N$ (X,Y) is a bivariate-Gaussian, neural weighting function. For a more complete definition and calculation of neural sharpness see Thibos et al., *Accuracy and precision of objective refraction from wave front aberrations*, Journal of Vision (2004) 4, 329-351, which discusses the problem of determining the best correction of an eye utilizing wave front aberrations. The wave front W(X,Y) of the contact lens and the eye is the sum of each as given by:

$$W_{CL+eye}(X,Y)=W_{CL}(X,Y)+W_{eye}(X,Y)^{EP,Rx}. \quad (3)$$

Wave front variations at different entrance pupil (EP) sizes and at different paraxial powers (Rx) are calculated based upon an excepted myopic progression rate over a specific time period. The effect of such wave front errors on neural sharpness can be determined. Accordingly, acceptable neural sharpness over the specific time period for a lens power profile can be ascertained by modeling and by clinical analysis. In specific embodiments, a difference in neural sharpness between a beginning of the time period and an end of the time period is about −0.1 to about −0.5 for either 4.5 mm or 6.5 mm entrance pupil size.

Figure 1A:
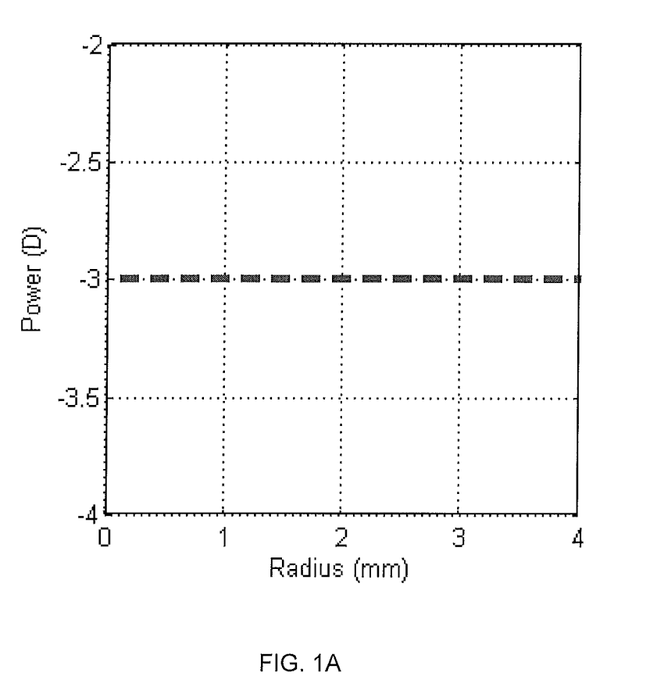
FIG. 1A is a power profile for a conventional spectacle spherical lens, for a subject starting spherical equivalent refractive error of −3.00 D.

With reference now to FIG. 1A, a conventional spectacle or contact lens power profile for a paraxial power of −3.00 D is illustrated. The power is relatively constant throughout the lens radial distance.

Figure 1B:
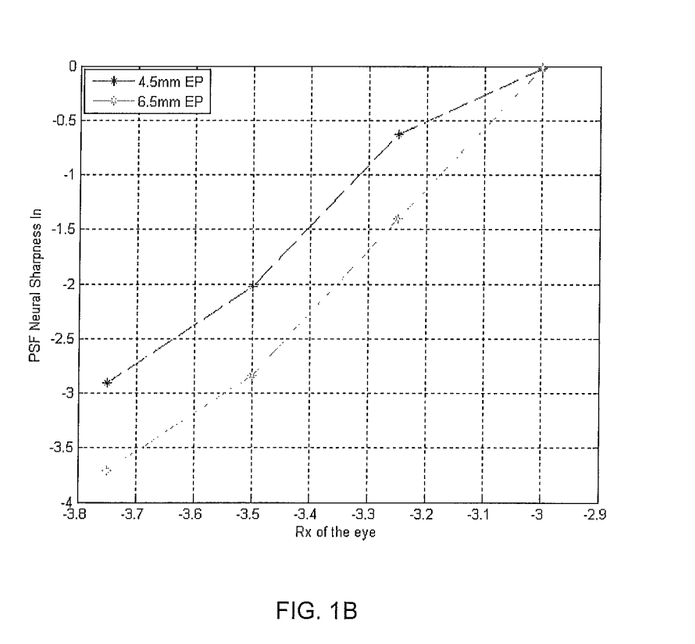
FIG. 1B is a graph showing neural sharpness versus myopic refractive error progression for the lens of FIG. 1A.

FIG. 1B is a graph showing neural sharpness changes versus myopic refractive error progression for the lens of FIG. 1A. As illustrated, the neural sharpness at −3.00 D (Rx at the beginning of the year) is optimal at the beginning of the year (initial fitting) and decreases sharply at the end of a year as the subject refraction changes to −3.75 D. The negative change (drop) in neural sharpness in this case exceeds 2.75 to 3.75 at entrance pupil diameters of 4.5 mm and 6.5 mm, respectively. Accordingly, a significant decrease in visual acuity is expected followed by increased dissatisfaction with the lens performance.

Figure 2A:
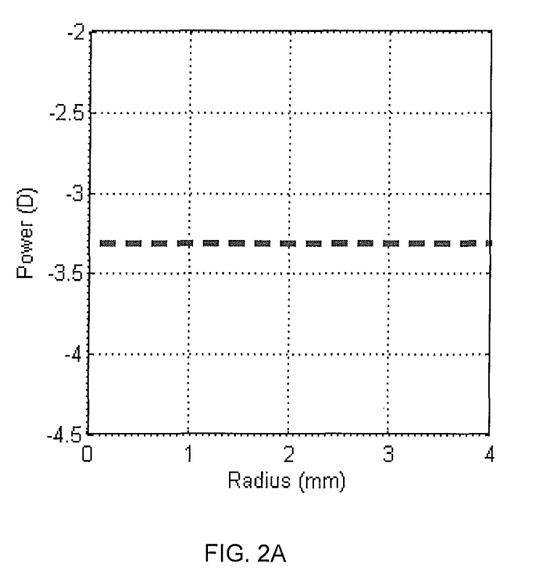
FIG. 2A is a power profile for a spherical ophthalmic lens according to the present invention, for a subject starting spherical equivalent refractive error of −3.00 D.

With reference now to FIG. 2A, a power profile is illustrated for a first ophthalmic lens design according to the present invention having no spherical aberration. The power may range from about 0.25 D to about 0.50 D less than a paraxial power (e.g., −3.00 D as shown). The power profile for the lens is determined by assuming a myopic progression rate over the course of a time period and determining acceptable neural sharpness. Assuming a myopic progression rate of −0.75 D/year, acceptable neural sharpness results in a power for the lens design of −3.32 D.

Figure 2B:
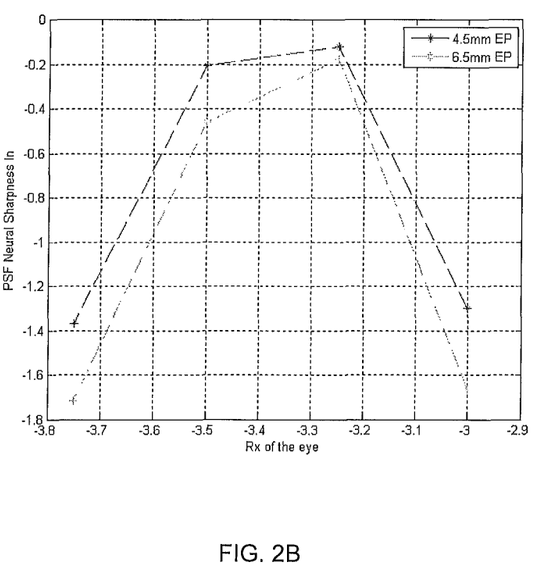
FIG. 2B is a graph showing neural sharpness versus myopic refractive error progression for the lens of FIG. 2A.

FIG. 2B is a graph showing neural sharpness changes versus myopic refractive error progression for the lens of FIG. 2A at entrance pupil sizes of 4.5 mm and 6.5 mm. As illustrated, the neural sharpness at −3.00 D (Rx at the beginning of the year) is similar to the neural sharpness at the end of a year (−3.75 D). Accordingly, changes in visual acuity variation are minimized.

Figure 3A:
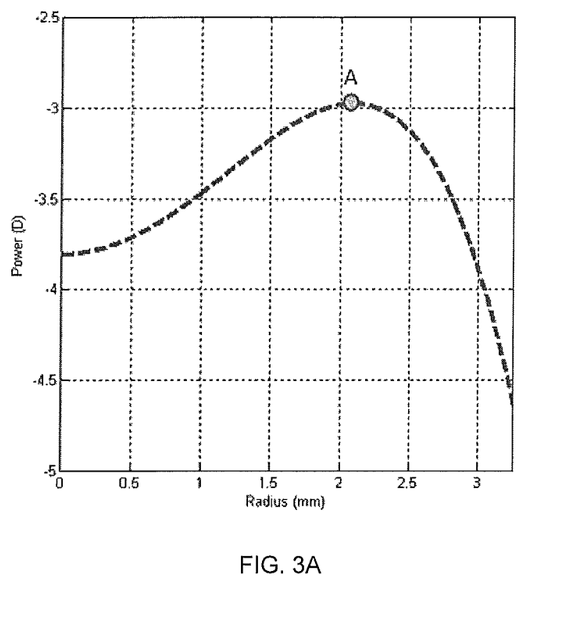
FIG. 3A is a power profile for an ophthalmic lens having spherical aberration according to the present invention, for a subject starting spherical equivalent refractive error of −3.00 D.

With reference now to FIG. 3A, a power profile is illustrated for a second ophthalmic lens design according to the present invention having spherical aberration. The power profile for the lens is determined by assuming a myopic progression rate of −0.75 D/year and determining acceptable neural sharpness.

The lens may have a power at the center of the lens that is less than paraxial power (for example, between −3.50 D to −4.00 D, which is less than a paraxial power of −3.00 D as shown in FIG. 3A). From the center of the lens, the dioptric power may increase to a point A. The power at point A may be between about −0.25 D and about +0.25 D around the paraxial power. The location of point A may be between about 1.75 mm and about 2.25 mm away from the center. Beyond point A, the power may drop to the margin of the pupil or optic zone. The magnitude of the drop may be between about 1.50 D to about 2.00 D.

Figure 3B:
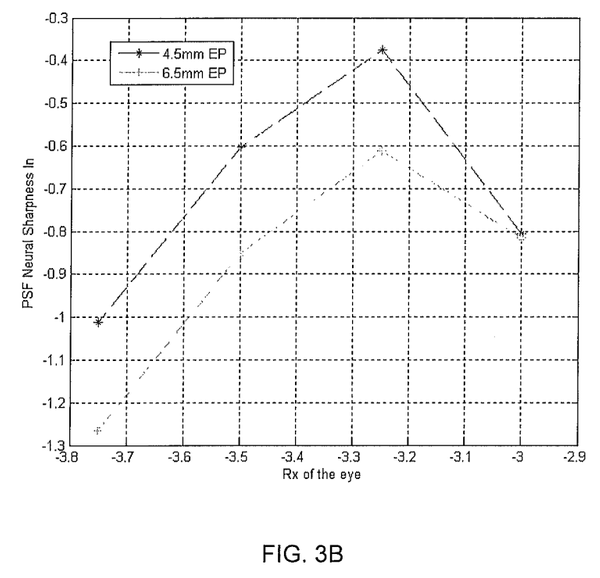
FIG. 3B is a graph showing neural sharpness versus myopic refractive error progression for the lens of FIG. 3A.

FIG. 3B is a graph showing neural sharpness changes versus myopic refractive error progression for the lens of FIG.

3A at entrance pupil sizes of 4.5 mm and 6.5 mm. As illustrated, the neural sharpness at −3.00 D (Rx at the beginning of the year) is similar to the neural sharpness at the end of a year (−3.75 D). Changes in visual acuity variation are minimized.

Figure 4A:
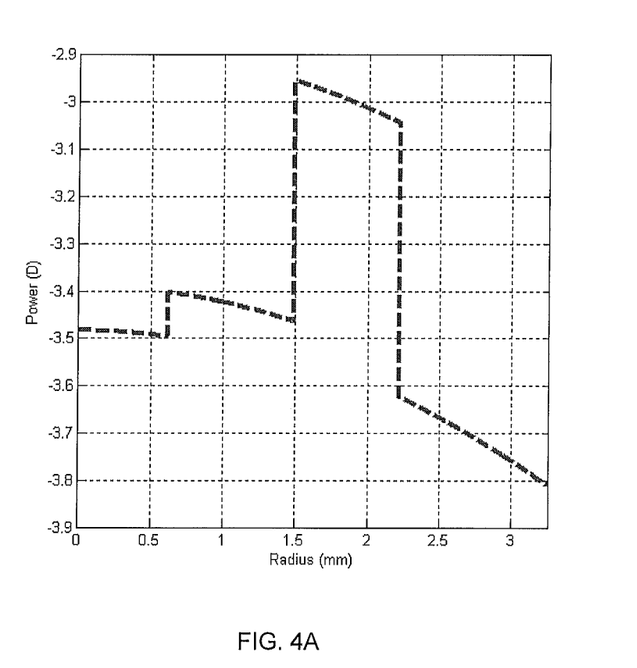
FIG. 4A is a power profile for a multifocal ophthalmic lens according to the present invention for a subject starting spherical equivalent refractive error of −3.00 D.

With reference now to FIG. 4A, a multifocal power profile is illustrated for a third ophthalmic lens design according to the present invention. The power profile may comprise two or more stepped or discontinuous zones. In the specific embodiment of FIG. 4A, the multifocal power profile comprises four zones and is determined by assuming a myopic progression rate of −0.75 D/year.

The power in the first stepped zone may be about 0.25 D to about 0.50 D less than the paraxial power (e.g., −3.00 D), and the width of the first stepped zone may be between about 0.5 mm to about 1.0 mm. The power in the second stepped zone may be about 0.1 OD more positive than the power of the first stepped zone and about 0.25 D to 0.50 D less than the paraxial power. The width of the second stepped zone may be between about 0.5 mm to about 1.0 mm. The power of the third stepped zone approximates a paraxial power of the eye (+/−0.25 D around −3.00 D) and has a width ranging from about 0.5 mm to about 1.0 mm. The power of the fourth stepped zone ranges between about 0.50 D to about 0.75 D less than the paraxial power.

A multifocal power profile lens design according to the present invention may also have negative spherical aberration. In specific embodiments, the magnitude of negative spherical aberration may range from about −0.03 D/mm$^2$ to about −0.10 D/mm$^2$.

Figure 4B:
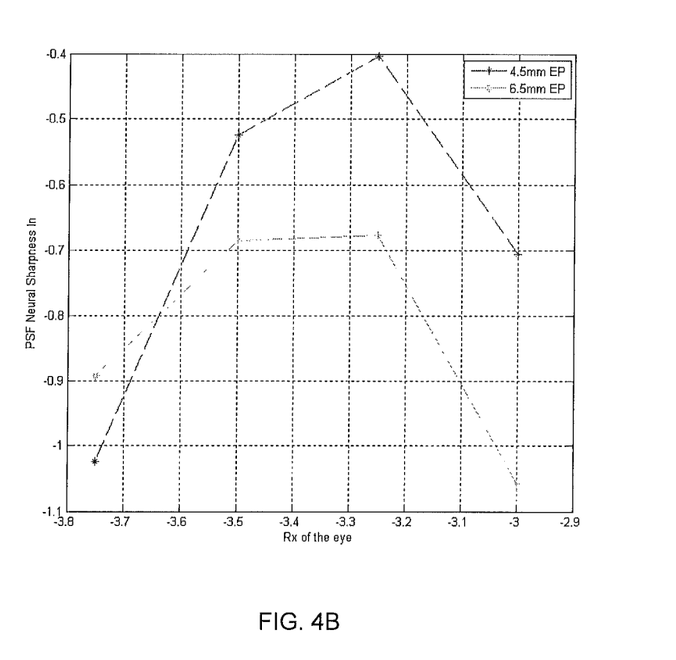
FIG. 4B is a graph showing neural sharpness versus myopic refractive error progression for the lens of FIG. 4A.

FIG. 4B is a graph showing neural sharpness changes versus myopic refractive error progression for the lens of FIG. 4A at entrance pupil sizes of 4.5 mm and 6.5 mm. As illustrated, the neural sharpness at −3.00 D (Rx at the beginning of the year) is similar to the neural sharpness at the end of a year (−3.75 D). Changes in visual acuity variation are therefore minimized.

Figure 5A:
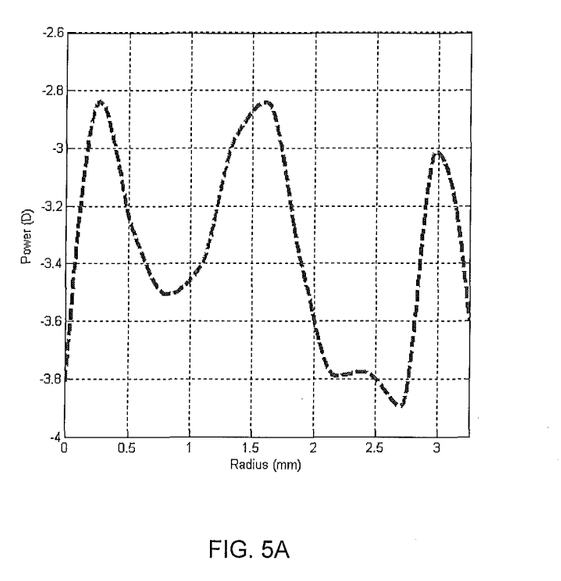
FIG. 5A is a power profile for a freeform ophthalmic lens according to the present invention, for a subject starting spherical equivalent refractive error of −3.00 D.

With reference now to FIG. 5A, a freeform power profile is illustrated for a fourth ophthalmic lens designs according to the present invention. The power profile for the lens is determined by assuming a myopic progression rate of −0.75 D/year and determining acceptable neural sharpness.

The power profile modulates between −1.00 D and +1.00 D, for example between −0.20 D and +0.80 D, around a paraxial power (e.g., −3.00 D). In the specific embodiment of FIG. 5A, the lens design has three peaks: a first peak at about 0.25 mm from the center of the lens, a second peak at about 1.6 mm from the center, and a third peak at about 3.0 mm from the center. A first valley is located between the first and second peaks, and a second valley is located between the second and third peaks. However, the number of peaks may vary and the distance between peaks may vary.

Figure 5B:
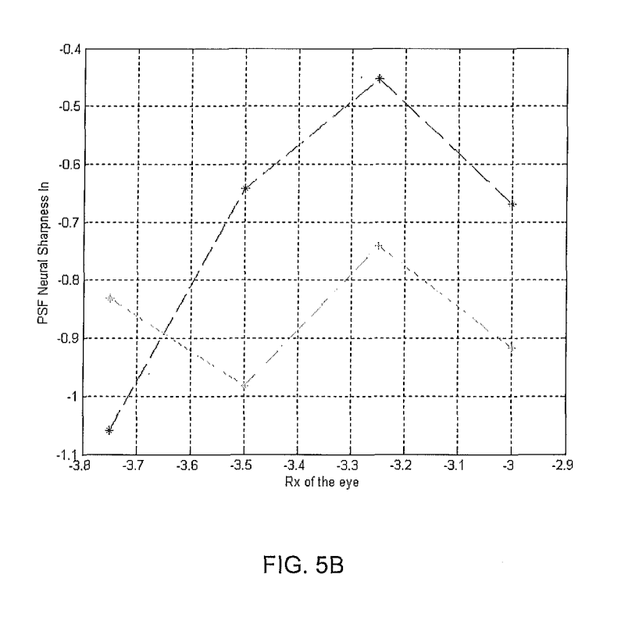
FIG. 5B is a graph showing neural sharpness versus myopic refractive error progression for the lens of FIG. 5A.

FIG. 5B is a graph showing neural sharpness changes versus myopic refractive error progression for the lens of FIG. 5A at entrance pupil sizes of 4.5 mm and 6.5 mm. As illustrated the neural sharpness at −3.00 D (Rx at the beginning of the year) is similar to the neural sharpness at the end of a year (−3.75 D).

Figure 6A:
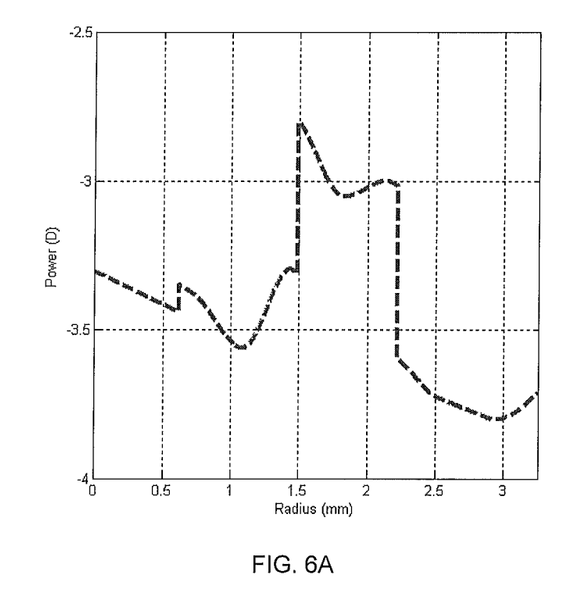
FIG. 6A is a power profile for a segmented freeform ophthalmic lens according to the present invention, for a subject starting spherical equivalent refractive error of a −3.00 D.

With reference now to FIG. 6A, a segmented freeform power profile is illustrated for a fifth ophthalmic lens design according to the present invention. The lens of FIG. 6A is a derivative of the lens of FIG. 4A, and is obtained by adding power modulation of +/−0.25 D on top of each of the four zones. Such modulation may be added to any number of zones.

Figure 6B:
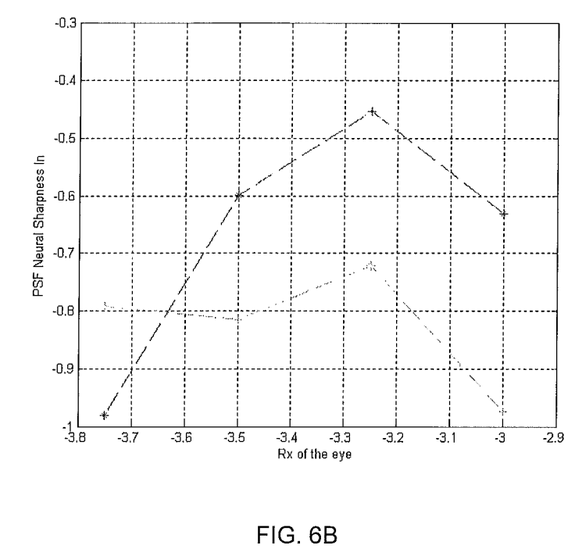
FIG. 6B is a graph showing neural sharpness versus myopic refractive error progression for the lens of FIG. 6A.

FIG. 6B is a graph showing neural sharpness changes versus myopic refractive error progression for the lens of FIG. 6A at entrance pupil sizes of 4.5 mm and 6.5 mm. As illustrated, the neural sharpness at −3.00 D (Rx at the beginning of the year) is similar to the neural sharpness at the end of a year (−3.75 D).

Figure 7:
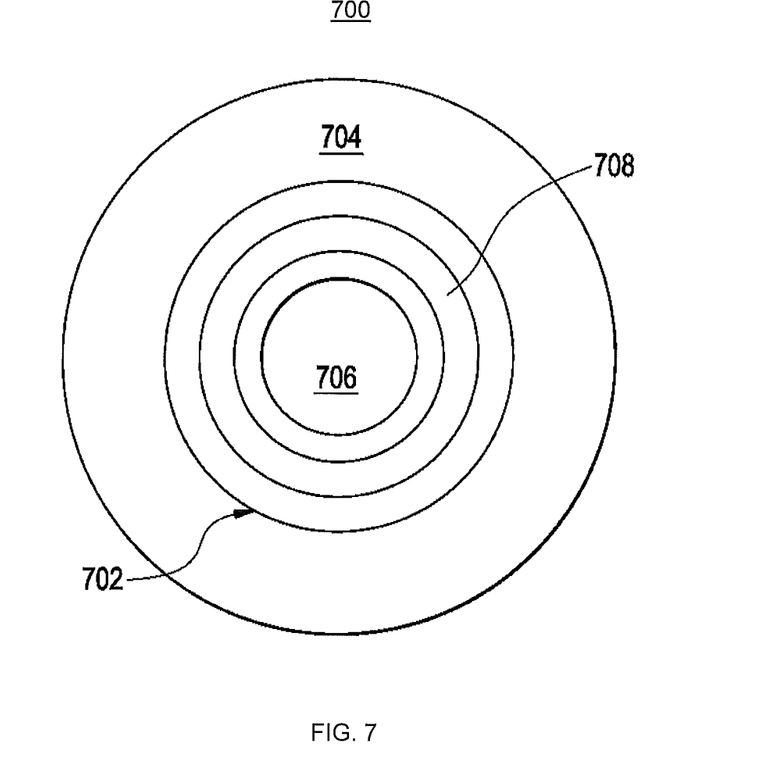
FIG. 7 is a diagrammatic representation of an exemplary contact lens in accordance with the present invention.

Referring to FIG. 7, there is illustrated a schematic diagrammatic view of a contact lens 700 in accordance with an embodiment of the present invention. The contact lens 700 comprises an optic zone 702 and an outer zone 704. The optic zone 702 comprises a first, central zone 706 and at least one peripheral zone 708. In specific embodiments, the diameter of the optic zone 702 may be selected to be 8.0 mm, the diameter of the substantially circular first zone 706 may be selected to be 4.0 mm, and the boundary diameters of an annular outer peripheral zone 708 may be 5 mm and 6.5 mm as measured from the geometric center of the lens 700. It is important to note that FIG. 7 only illustrates an exemplary embodiment of the present invention. For example, in this exemplary embodiment, the outer boundary of the at least one peripheral zone 708 does not necessarily coincide with the outer margin of the optic zone 702, whereas in other exemplary embodiments, they may coincide. The outer zone 704 surrounds the optic zone 702 and provides standard contact lens features, including lens positioning and centration. In accordance with one exemplary embodiment, the outer zone 704 may include one or more stabilization mechanisms to reduce lens rotation when on eye.

It is important to note that the various zones in FIG. 7 are illustrated as concentric circles, the zones may comprise any suitable round or non-round shapes such as an elliptical shape.

It is important to note that as the entrance pupil size of the eye varies among subpopulations, in certain exemplary embodiments, the lens design may be customized to achieve both good foveal vision correction and myopic treatment efficacy based on the patient's average pupil size. Moreover, as pupil size correlates with refraction and age for pediatric patients, in certain exemplary embodiments, the lens may be further optimized towards subgroups of the pediatric subpopulation with specific age and/or refraction based upon their pupil sizes. Essentially, the power profiles may be adjusted or tailored to pupil size to achieve an optimal balance between foveal vision correction and minimization of visual acuity over time across a range of pupil sizes.

Currently available contact lenses remain a cost effective means for vision correction. The thin plastic lenses fit over the cornea of the eye to correct vision defects, including myopia or nearsightedness, hyperopia or farsightedness, astigmatism, i.e. asphericity in the cornea, and presbyopia, i.e., the loss of the ability of the crystalline lens to accommodate. Contact lenses are available in a variety of forms and are made of a variety of materials to provide different functionality.

Daily wear soft contact lenses are typically made from soft polymer materials combined with water for oxygen permeability. Daily wear soft contact lenses may be daily disposable or extended wear disposable. Daily disposable contact lenses are usually worn for a single day and then thrown away, while extended wear disposable contact lenses are usually worn for a period of up to thirty days. Colored soft contact lenses use different materials to provide different functionality. For example, a visibility tint contact lens uses a light tint to aid the wearer in locating a dropped contact lens, enhancement tint contact lenses have a translucent tint that is meant to enhance one's natural eye color, the color tint contact lens comprises a darker, opaque tint meant to change one's eye color, and the light filtering tint contact lens functions to enhance certain colors while muting others. Rigid gas permeable hard contact lenses are made from siloxane-containing polymers but are more rigid than soft contact lenses and thus hold their shape and are more durable. Bifocal contact lenses are designed specifically for patients with presbyopia and are available in both soft and rigid varieties. Toric contact lenses are designed specifically for patients with astigmatism and are also available in both soft and rigid varieties. Combination lenses combining different aspects of the above are also available, for example, hybrid contact lenses.

It is important to note that the lens designs of the present invention may be incorporated into any number of different contact lenses formed from any number of materials. Specifically, the lens design of the present invention may be utilized in any of the contact lenses described herein, including, daily wear soft contact lenses, rigid gas permeable contact lenses, bifocal contact lenses, toric contact lenses and hybrid contact lenses. In addition, although the invention is described with respect to contact lenses, it is important to note that the concept of the present invention may be utilized in spectacle lenses, intraocular lenses, corneal inlays and onlays.

Although shown and described is what is believed to be the most practical and preferred embodiments, it is apparent that departures from specific designs and methods described and shown will suggest themselves to those skilled in the art and may be used without departing from the spirit and scope of the invention. The present invention is not restricted to the particular constructions described and illustrated, but should be constructed to cohere with all modifications that may fall within the scope of the appended claims.

What is claimed is:

1. An ophthalmic lens for minimizing visual acuity variation for a progressing myope comprising a lens having a center and at least one peripheral zone surrounding the center and having a different dioptric power than at the center,
wherein said lens has power profile is selected from the group consisting of a power profile with spherical aberration, a multifocal power profile, a freeform power profile, and a segmented freeform power profile, said power profile being determined based on an initial paraxial power of a progressing myope and a defined myopia progression rate over a specific time period such that a difference in neural sharpness over the specific time period is between −0.1 and −0.5, so that changes in visual acuity at a beginning of said time period and at an end of said time period are minimized.

2. The ophthalmic lens according to claim 1, wherein the defined myopic progression rate is from about −0.25 D/year to −0.75 D/year.

3. The ophthalmic lens according to claim 1, wherein the power profile has a spherical aberration and wherein a power at the center of the lens is more negative than a paraxial power and increases to a point in the at least one peripheral zone that corresponds to the paraxial power.

4. The ophthalmic lens according to claim 1, wherein the power profile comprises a multifocal power profile having two or more stepped or discontinuous peripheral zones.

5. The ophthalmic lens according to claim 4, wherein a first stepped peripheral zone surrounding the center of the lens has a power less than a paraxial power and a second stepped peripheral zone has a dioptric power of +/−0.25 D of the paraxial power.

6. The ophthalmic lens according to claim 1, wherein the power profile comprises a freeform power profile having a plurality of peaks that modulate between −0.20 D and +0.80 D around a paraxial power.

7. The ophthalmic lens according to claim 6, wherein the power profile comprises three peaks in the at least one peripheral zone.

8. The ophthalmic lens according to claim 1, wherein a difference in neural sharpness between the beginning of said the time period and the end of said time period is about −0.1 to about −0.5 for an entrance pupil diameter of 4.5 mm or 6.5 mm.

9. The ophthalmic lens according to claim 1, wherein the ophthalmic lens comprises a contact lens.

10. The ophthalmic lens according to claim 1, wherein the ophthalmic lens comprises an intraocular lens, a corneal inlay, or a corneal onlay.

11. The ophthalmic lens according to claim 1, further comprising one or more stabilization mechanisms.

12. A method for minimizing visual acuity variation for a progressing myope, comprising:
providing an ophthalmic lens having a center and at least one peripheral zone surrounding the center and having a different dioptric power than at the center, said lens having a power profile selected from the group consisting of a power profile with spherical aberration, a multifocal power profile, a freeform power profile, and a segmented freeform power profile; and
determining the power profile of the lens based on a paraxial power of a progressing myope and a defined myopia progression rate over a specific time period such that a difference in neural sharpness over the specific time period is between −0.1 and −0.5, thereby minimizing changes in changes in visual acuity at a beginning of said time period and at an end of said time period.

13. A method according to claim 12, wherein the myopia progression rate is selected based on at least one of gender, age, ethnicity, or family history of the progressing myope.

14. A method according to claim 12, wherein myopia progression ranges from about −0.25 D/year to −0.75 D/year.

15. A method according to claim 12, wherein the power profile has a spherical aberration and a power at the center of the lens is less than a paraxial power and increases to a point in the at least one peripheral zone that corresponds to the paraxial power.

16. The method according to claim 12, wherein the power profile comprises a multifocal power profile having two or more stepped or discontinuous peripheral zones.

17. The method according to claim 16, wherein a first stepped peripheral zone surrounding the center of the lens has a power less than a paraxial power and second stepped peripheral zone has a dioptric power of +/−0.25 D of the paraxial power.

18. The method according to claim 12, wherein the power profile is a continuous freeform power profile and has a plurality of peaks that modulate between −0.20 D and +0.80 D around a paraxial power.

19. The method according to claim 18, wherein the power profile comprises three peaks in the at least one peripheral zone.

20. The method according to claim 12, wherein a difference in neural sharpness between the beginning of said the time period and the end of said time period is about −0.1 to about −0.5 for an entrance pupil diameter of 4.5 mm or 6.5 mm.

21. The method according to claim 12, wherein the ophthalmic lenses comprises a contact lens.

22. The method according to claim 12, wherein the ophthalmic lens comprises an intraocular lens, a corneal inlay, or a corneal onlay.

23. The method according to claim 12, further comprising adding one or more stabilization mechanisms to the ophthalmic lens.

* * * * *